United States Patent
Barnicki et al.

(10) Patent No.: US 6,596,882 B2
(45) Date of Patent: *Jul. 22, 2003

(54) RECOVERY AND PURIFICATION OF 3,4-EPOXY-1-BUTENE USING WATER-MISCIBLE SOLVENTS

(75) Inventors: Scott Donald Barnicki, Kingsport, TN (US); Jerome Leonard Stavinoha, Jr., Longview, TX (US); Robert Sterling Kline, Talbott, TN (US); Steven Edward Briley, Longview, TX (US); Jackie Lee Hamilton, Jonesborough, TN (US)

(73) Assignee: Eastman Chemical Company, Kingsport, TN (US)

( * ) Notice: Subject to any disclaimer, the term of this patent is extended or adjusted under 35 U.S.C. 154(b) by 5 days.

This patent is subject to a terminal disclaimer.

(21) Appl. No.: 09/910,332

(22) Filed: Jul. 20, 2001

(65) Prior Publication Data

US 2003/0060644 A1 Mar. 27, 2003

(51) Int. Cl.$^7$ .................. C07D 301/32; C07D 301/10
(52) U.S. Cl. ........................... 549/538; 549/541
(58) Field of Search ................. 549/538, 541

(56) References Cited

U.S. PATENT DOCUMENTS

| | | |
|---|---|---|
| 2,773,844 A | 12/1956 | Carlson et al. |
| 3,418,338 A | 12/1968 | Gilman et al. |
| 3,644,432 A | 2/1972 | Hoch et al. |
| 3,745,092 A | 7/1973 | Vanderwater |
| 3,948,621 A | 4/1976 | Cocuzza et al. |
| 3,962,136 A | 6/1976 | Nielsen et al. |
| 3,964,980 A | 6/1976 | Ozero |
| 4,221,727 A | 9/1980 | Tsang et al. |
| 4,233,221 A | 11/1980 | Raines et al. |
| 4,356,312 A | 10/1982 | Nielsen et al. |
| 4,437,938 A | 3/1984 | Bhise et al. |
| 4,437,939 A | 3/1984 | Bhise et al. |
| 4,897,498 A | 1/1990 | Monnier et al. |
| 4,950,773 A | 8/1990 | Monnier et al. |
| 5,081,096 A | 1/1992 | Monnier et al. |
| 5,117,012 A | 5/1992 | Stavinoha, Jr. et al. |
| 5,312,931 A | 5/1994 | Stavinoha, Jr. |
| 5,529,667 A | 6/1996 | Coffey |
| 5,559,255 A | 9/1996 | Kawabe et al. |
| 5,618,954 A | 4/1997 | Boeck et al. |
| 5,756,779 A | 5/1998 | Stavinoha, Jr. |
| 6,018,061 A | 1/2000 | Barnicki et al. |
| 6,172,245 B1 | 1/2001 | Monnier et al. |
| 6,395,913 B1 | 5/2002 | Barnicki et al. |

FOREIGN PATENT DOCUMENTS

GB          864882          4/1961

OTHER PUBLICATIONS

Dever et al., Ethylene Oxide, Kirk–Othmer Encyclopedia of Chemical Technology, 4th Ed., vol. 9, 1994, pp. 925–939.
Kister, H. Z. Distillation Design, McGraw–Hill, N.Y. (1992), Chapter 6.
Kister, H. Z. Distillation Design, McGraw–Hill, N.Y. (1992), Chapter 8.

*Primary Examiner*—Ba K. Trinh
(74) *Attorney, Agent, or Firm*—Michael J. Blake; Bernard J. Graves, Jr.

(57) ABSTRACT

Disclosed is a method of recovering and purifying 3,4-epoxy-1-butene (epoxybutene) from an epoxidation effluent gas obtained by the vapor phase, catalytic, partial oxidation of 1,3-butadiene (butadiene) with molecular oxygen in the presence of a silver catalyst wherein the epoxybutene-laden epoxidation product gas is reacted with a water-miscible solvent to absorb the epoxybutene. The disclosed process includes a method of separating epoxybutene from the solvent and other reaction by-products by a novel combination of distillation and decantation steps.

6 Claims, 1 Drawing Sheet

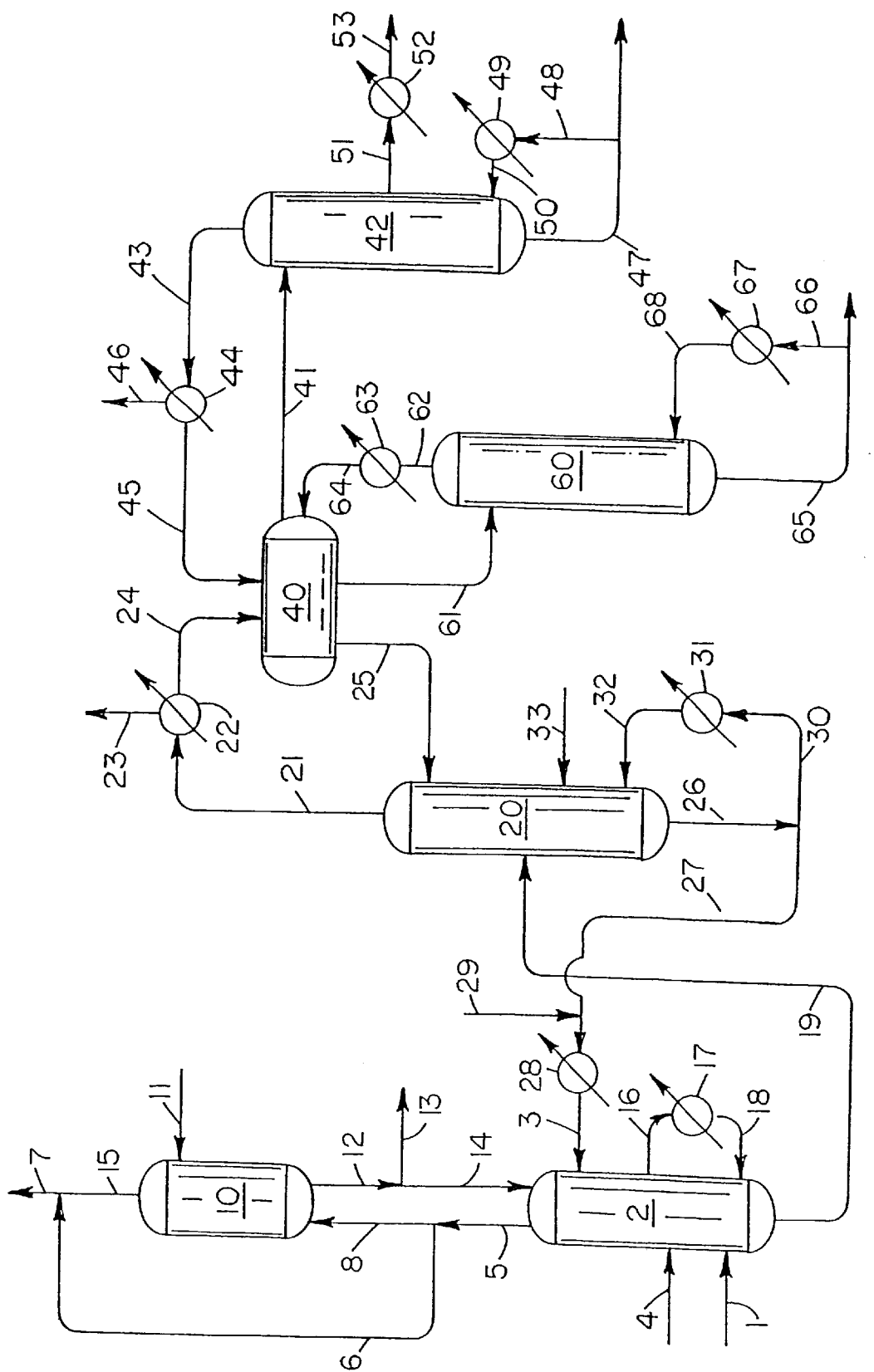
Fig.

RECOVERY AND PURIFICATION OF 3,4-EPOXY-1-BUTENE USING WATER-MISCIBLE SOLVENTS

FIELD OF THE INVENTION

The present invention relates to a method of recovering and purifying 3,4-epoxy-1-butene (epoxybutene) from an epoxidation effluent gas obtained by the vapor phase, catalytic, partial oxidation of 1,3-butadiene (butadiene) with molecular oxygen in the presence of a silver catalyst. More specifically, the present invention relates to a method of recovering epoxybutene from an epoxybutene-laden reaction product gas by absorption into a water-miscible solvent. This invention also relates to a method of separating epoxybutene from the solvent and other reaction by-products by a novel combination of distillation and decantation steps.

BACKGROUND OF THE INVENTION

Ethylene oxide (EO) and 1,2-epoxy-3-butene both are produced by processes which involve the catalytic, partial oxidation of the corresponding olefin, i.e., ethylene and butadiene, with oxygen in the presence of a silver catalyst. See, for example, U.S. Pat. Nos. 2,773,844 and 3,962,136, and 4,356,312 for ethylene oxide oxidation and U.S. Pat. Nos. 4,897,498, 4,950,773, and 5,081,096 for butadiene oxidation. Considerable effort has been devoted to the development of efficient methods for recovering these epoxides, particularly EO, from the reaction product gas and subsequent purification of the epoxide.

According to U.S. Pat. Nos. 3,745,092 and 3,964,980, and Dever et al *Ethylene Oxide*, in *Kirk-Othmer Encyclopedia of Chemical Technology*, 4$^{th}$ Ed., 1994, pages 929–930, EO is recovered and purified according to the following procedure. A reaction product gas typically containing 0.5 to 5% EO, obtained by the vapor phase, catalytic oxidation of ethylene with molecular oxygen in the presence of a silver catalyst, is introduced to an EO absorption tower wherein it is contacted counter-currently with an absorbent comprised primarily of water which absorbs the ethylene oxide. The absorber typically is maintained at a temperature of 5 to 40° C. and a pressure of 10 to 30 bar absolute (bara).

The EO-laden absorbent then is transferred to a distillation (stripping) column wherein vaporous EO is recovered from the upper section or top of the tower at a temperature of 85 to 140° C. by steam stripping at reduced pressure. The water remaining after the distillation of EO is recycled to the absorption tower for reuse. EO reacts readily with water under absorption and distillation conditions to form ethylene glycol, which can react further to form diethylene glycol, triethylene glycol, and higher oligomers. Although ethylene glycol is a valuable and marketable chemical, diethylene glycol and higher oligomers have much less commercial demand and, thus, normally are undesirable by-products. Formation of ethylene glycol oligomers can be controlled to some extent by limiting ethylene glycol concentration in the recycled water to the absorber. Typical levels are less than 10 weight per cent ethylene glycol in the recycled absorber water.

The crude EO vapor recovered in the stripper overhead comprises EO as the main component, as well as impurities such as water, argon, nitrogen, carbon dioxide, methane, ethane and ethylene, formaldehyde, and acetaldehyde. This crude EO vapor is fed to a second distillation (stripping) column from which the light or low-boiling components, e.g., nitrogen, carbon dioxide, argon, methane, ethane, and ethylene, are removed from the upper section or top of the column. A partially purified EO is removed from the lower section or base of the second stripping column and is transferred to the mid-section of a refining column for final purification. U.S. Pat. Nos. 5,529,667 and 3,418,338 disclose the use of extractive distillation with water as a solvent in either the second stripping column or the refining column to reduce the level of aldehyde impurities in the final purified ethylene oxide product.

By employing the above-described procedure, EO purities of greater than 99.5 mole per cent are possible. Although the water-based processing procedure functions effectively for EO recovery and purification, it cannot be employed equally efficaciously for the recovery and purification of epoxybutene. Firstly, whereas ethylene oxide is completely and infinitely miscible with water, epoxybutene is only sparingly miscible with water. At 25° C. the solubility of epoxybutene in water is only about 5 to 6 weight percent. As a result, water is a very poor absorbent for epoxybutene. High water to epoxybutene ratios, i.e., upward of 50/1 to 150/1, are required to ensure complete absorption of epoxybutene from the butadiene oxidation effluent. The use of such ratios is prohibited by the cost of the equipment and energy required.

Secondly, EO is a relatively low-boiling component compared to water, i.e., normal boiling point of 10.4° C. versus 100° C., respectively, and does not form an azeotrope with water. Thus, EO can be distilled readily from water by simple fractional distillation techniques as described above for the conventional EO recovery scheme. However, epoxybutene is much more hydrophobic than EO oxide and forms a minimum-boiling azeotrope with water. High purity epoxybutene cannot be obtained by the simple fractional distillation techniques employed for EO recovery.

Other methods proposed for recovery of EO from ethylene oxidation effluents likewise are not effective or are uneconomical for epoxybutene recovery and purification. For example, U.S. Pat. No. 3,948,621 discloses a method of separating EO and carbon dioxide simultaneously from a mixed gas obtained from catalytic oxidation of ethylene using methanol as an absorbent. As with water, epoxybutene forms a minimum-boiling azeotrope with methanol and thus epoxybutene and methanol cannot be separated readily by simple fractional distillation.

U.S. Pat. Nos. 4,437,938 and 4,437,939 disclose methods using supercritical or near supercritical carbon dioxide and water at the same time as absorbents. EO is first absorbed into water as in conventional recovery methods. The EO-rich aqueous absorbent is contacted with (near) supercritical carbon dioxide, and EO is extracted to the carbon dioxide solvent. The carbon dioxide is separated from EO by distillation under reduced pressure. The carbon dioxide is recompressed before recycling as the extraction solvent. This method, however, has many drawbacks. First, the required amount of (near) supercritical carbon dioxide is approximately 35 times the amount of EO to be absorbed therein, which requires large equipment. The extraction is carried out at high pressures, i.e., 86 bara, while the distillation step is carried out at lower pressure, i.e., about 0.1 to 2 bara. The wide pressure differential results in high compression costs and thus does not provide an economical solution.

U.S. Pat. Nos. 4,221,727 and 4,233,221 discloses an EO recovery method that uses ethylene carbonate as an absorbent for EO. Ethylene carbonate has many advantages as an absorbent. The absorption affinity of ethylene carbonate for EO is higher than that of water. The vapor pressure of ethylene carbonate is quite low, i.e., normal boiling point of 239° C., so losses into the recycle gas are minimal. Moreover, ethylene carbonate is stable and does not react directly with EO. The process disclosed in U.S. Pat. No. 4,233,221, however, has the following drawbacks for EO and epoxybutene recovery. The most preferred temperature range for operation of conventional absorption of EO with water is 5 to 40° C. The melting point of ethylene carbonate is 39° C., so ethylene carbonate would be a solid over almost all of the preferred temperature range. In order to avoid solidification, it is necessary to operate the absorber and other processing equipment substantially above, i.e., at least 10 to 20° C., above the melting point of ethylene carbonate. This is much higher temperature than an operation using water. The absorbing power of the ethylene carbonate correspondingly decreases so that the amount of circulating absorbent must be increased, reducing the economic utility of the process.

U.S. Pat. No. 5,559,255 describes the use of propylene carbonate as an absorbent for EO. The EO-laden propylene carbonate is stripped with an inert gas to recover ethylene oxide and the water by-product from the epoxidation reactor as a vapor. Purified EO is produced from the mixed water-EO vapors as in conventional methods described in U.S. Pat. Nos. 3,745,092 and 3,964,980. Unlike ethylene carbonate, propylene carbonate is a liquid at room temperature and thus offers a more robust process than ethylene carbonate absorption. However, the process described In U.S. Pat. No. 5,559,255 also has drawbacks for epoxybutene recovery and purification. Epoxybutene is a much less volatile component than ethylene oxide and cannot be removed effectively from propylene carbonate by inert gas stripping as described in the '255 patent. Moreover, this EO process does not presage or address the problems associated with epoxybutene recovery and separation from the epoxybutene-water azeotrope, butadiene, or other impurities absorbed with epoxybutene from the butadiene epoxidation reactor product gas.

U.S. Pat. No. 3,644,432 discloses the use of liquid ethane as an absorbent for EO. The reactor product gas is cooled, compressed, and then passed through a molecular sieve drier bed to remove the by-product water of reaction. The dried reactor product gas is contacted in a countercurrent absorption tower with liquid ethane at a preferred temperature range of −31.5 to −17.6° C. at a pressure of about 1.8 MPa. EO is much more soluble in liquid ethane than in water, so the solvent to feed gas ratio of the absorber can be reduced considerably from the water absorbent case, with concomitant cost reductions. However, maintenance of such cryogenic temperatures requires expensive refrigeration equipment and which more than offsets any savings due to lower solvent to feed gas ratios. Thus, there are no acceptable absorption/separation methods originally developed for EO that can be adapted readily and economically to epoxybutene absorption/separation.

The patent literature is not as extensive for epoxybutene production, but several patents address the issue of epoxybutene recovery/separation. U.S. Pat. Nos. 5,117,012 and 5,312,931 disclose the use of liquid butadiene and butadiene/butane mixtures as an absorbent for epoxybutene. The reactor product gas is cooled, compressed, and contacted in a countercurrent absorption tower with liquid butadiene/n-butane at a preferred temperature range of 0 to 30° C. at a pressure of about 5 to 15 bar. Water and water-soluble impurities are removed by decantation of the epoxybutene-rich absorbent stream. Any remaining water, butadiene/n-butane absorbent, and low-boiling impurities are removed by distillation to give a purified epoxybutene product. However, n-butane and 1,3-butadiene have relatively high volatilities, with normal boiling points of −0.5° C. and −4.5° C., respectively. In order to ensure that substantially all of the solvent n-butane/butadiene remains a liquid within the absorption zone at operating temperatures that can be achieved with an inexpensive cooling medium such as water, i.e., above at least about 30° C., the absorption zone must be operated at a pressure of at least about 4.2 bars. Operation at lower pressures, and concomitantly lower temperatures is quite costly if the required low temperature cooling is supplied by ordinary means known to those skilled in the art such as chilled brine or glycol refrigeration units. Thus, to meet the aforementioned temperature and pressure requirements for absorption with n-butane, the reactor effluent must first be compressed to a suitable pressure, i.e., greater than about 4.2 bars, prior to its introduction into the absorption zone. The higher pressures and resulting polytropic temperature rise within the compression zone in the presence of high concentrations of epoxybutene can cause formation of polymeric materials that deposit on the walls of the compressor and associated piping. The build-up of such polymeric material reduces the operating efficiency of the compressor and can lead to permanent equipment damage and frequent process shutdowns for maintenance, with subsequent loss of production and revenues. Moreover, the large inventory in the absorption/distillation of highly volatile and explosive butadiene and butane is dangerous and leads to higher than average safety-related costs.

U.S. Pat. No. 6,018,061 addresses the problems inherent with the compression of high concentrations of epoxybutene, as exemplified in U.S. Pat. Nos. 5,117,012 and 5,312,931, by providing a compression or absorption refrigeration cycle for cooling the epoxybutene absorption zone prior to compression with the reaction diluent, i.e., C3 to C5 hydrocarbons, preferably butane/butadiene, as the refrigerant. In this fashion, the epoxybutene absorption zone can be operated at pressures less than about 4 bar and a temperature of less than about 40° C. without need for pre-compression or external refrigeration. However, with pressures in the absorption zone higher than the 4 bars specified in the '061 patent, the auto-cooling effect provided by the refrigeration cycle is greatly diminished. The temperature of the absorber becomes hotter and the absorptive power of the solvent, i.e., butane/butadiene, is greatly reduced. Thus, for example, at a pressure of about 5.5 bara (80 pounds per square inch-psia), the auto-refrigeration effect provides only a temperature of about 60° C. Moreover, at pressures above 4 bar, the potential for unwanted condensation of n-butane/butadiene in equipment in the recycle loop increases dramatically. Excessive condensation can cause the recycle gas composition to become flammable, an unsafe and unacceptable operating condition. Finally, as with the '012 and '931 patents, the required inventory of highly volatile and explosive butadiene and butane is large.

U. S. Pat. No. 5,618,954 discloses the recovery of epoxybutene from a butadiene epoxidation reactor effluent gas by countercurrent contact in an absorption zone using a solvent comprising water as a primary component. Epoxybutene is recovered from the water by stripping with an inert gas, similar to the conventional EO recovery process described above. As explained above, water by itself is a poor absorbent for epoxybutene and its use results in an uneconomical process due to the required high water to epoxybutene ratio. Moreover, the process, as described in the '954 patent is incomplete and cannot provide purified epoxybutene. No mention is made of the binary epoxybutene-water minimum-boiling azeotrope or of methods to obtain purified epoxybutene from this azeotrope with water.

In view of the recovery processes described above, it is apparent that there is a need for an improved process for the efficient and economical recovery and purification of epoxybutene from a butadiene epoxidation effluent, i.e., the product gas of a vapor phase epoxidation reactor.

SUMMARY OF THE INVENTION

It has been discovered that epoxybutene can be recovered from a substantially vaporous epoxidation effluent comprising epoxybutene, oxygen, unreacted butadiene, and inert reaction diluent, e.g., methane, ethane, nitrogen, and the like, by intimately contacting the vaporous effluent with an effective amount of a water-miscible, liquid absorbent or solvent in a first absorption zone, such as an absorber, to absorb essentially all of the epoxybutene present in the vaporous reactor effluent. The present invention therefore provides a process for the recovery of epoxybutene from a substantially-gaseous effluent from an epoxidation zone wherein butadiene is contacted with an oxygen-containing gas in the presence of a catalyst and an inert diluent, to produce an epoxidation effluent comprising epoxybutene, butadiene, oxygen, an inert diluent and water which comprises feeding the effluent to an absorption vessel wherein the effluent is intimately contacted with a water-miscible, liquid absorbent to obtain:

(1) a gaseous effluent comprising butadiene, oxygen and an inert diluent from the upper section of the absorption vessel; and (2) a liquid effluent comprising epoxybutene, the absorbent and water from the lower section of the absorption vessel; wherein the absorbent is selected from diols, aliphatic and cyclic ethers, alkoxyalkanols, alkanoate esters of alkoxyalkanols, dialkoxyalkanes, alkylnitriles, N,N-dialkylformamides, N,N-dialkylacetamides, N-alkylpyrrolidinones, dialkyl sulfoxides, morpholine, pyridine, or a mixture of any 2 or more thereof and the absorbent compound(s) contain 3 to about 8 carbon atoms; epoxybutene is 3,4-epoxy-1-butene; and butadiene is 1,3-butadiene.

A second embodiment of the present invention provides for the recovery of epoxybutene from the above liquid effluent (2) by the steps of:

I. feeding liquid effluent (2) to the middle section of a first distillation column to obtain (1) a distillate effluent comprising epoxybutene and water from the upper section of the distillation vessel; and (2) a liquid effluent comprising the absorbent and water from the lower section of the distillation vessel;

II. allowing distillate (1) from step I to form 2 phases comprising an epoxybutene-rich phase and a water-rich phase; and III. feeding the epoxybutene-rich phase from step II to the upper section of a second distillation column to obtain (1) a distillate effluent comprising epoxybutene and water from the upper section of the distillation vessel; and (2) a liquid effluent comprising the epoxybutene from the lower section of the distillation vessel.

Additional embodiments of the invention include the refining of the water-rich phase obtained from step II and the removal of absorbent present in effluent comprising butadiene, oxygen and an inert diluent from the upper section of the absorption vessel.

BRIEF DESCRIPTION OF THE DRAWING

The accompanying FIGURE is a process flow diagram illustrating an epoxybutene recovery system embodying the principles of the processes of the present invention. While the present invention is susceptible to embodiment in various forms, there is shown in the FIGURE and hereinafter described in detail preferred embodiments of the invention. However, the present disclosure is to be considered as an exemplification of the invention without limitation to the specific embodiments illustrated.

DETAILED DESCRIPTION OF THE INVENTION

The process of the present invention may be used in combination with any epoxidation process wherein butadiene is contacted with an oxygen-containing gas in the presence of a catalyst and an inert gas to produce a gaseous, epoxidation effluent comprising epoxybutene, oxygen, unreacted butadiene, and reaction diluent, e.g., nitrogen, carbon dioxide, methane, ethane, propane, n-butane, or other species inert under reaction conditions. The silver-catalyzed, epoxidation processes described in U.S. Pat. Nos. 4,897,498 and 4,950,773 are typical of those that may be employed in the epoxidation zone. The epoxidation zone comprises one or more reactors of any design that allows removal of the heat of reaction in order to prevent an exothermic temperature excursion from occurring. For example, a shell-and-tube design, typically used for ethylene oxide production, may be employed. Other types of reactor designs include multi-staged adiabatic reactors, fluidized bed reactors, moving or transport bed reactors and the like.

The feed to the epoxidation zone comprises butadiene, an oxygen-containing gas and an inert diluent gas in various proportions. Generally, any oxygen ($O_2$) concentration up to the explosive limit can be used. For example, when using nitrogen as the inert gas, the maximum oxygen concentration normally is in the range of about 9 mole percent. Higher oxygen concentration, e.g., up to about 18 mole percent, may be employed using methane as the inert diluent. When using butane as the inert diluent gas, relatively high oxygen concentrations, e.g., up to about 30 mole percent may be employed. The recovery process of the present invention advantageously is used in combination with a butadiene epoxidation process employing carbon dioxide, nitrogen, ethane, or preferably, methane as the inert diluent. The butadiene concentration typically is about 4 to 50 mole percent. The butadiene:oxygen mole ratio in the feed normally is maintained within the range of about 1:5 to 10:1. The inert gas usually constitutes about 25 to 85 mole percent of the total feed to the epoxidation zone. Normally, the feed also includes a small amount, e.g., 1 to 40 parts per million (ppm), of a halide source such as 1,2-dichloroethane. Various other organic halides may be used, many of which are described in U.S. Pat. No. 4,950,773. The concentration of the organic halide in the feed more commonly is in the range of 2 to 10 ppm. The feed also may contain minor amounts, e.g., 5 mole percent or greater, of impurities such as up to about 4 mole percent water and up to 2 mole percent carbon dioxide. Some argon may also be present in the feed. The amount of argon is controlled by purging a small amount of the recycle gas. Typically, the amount of argon is maintained at less than 10 percent.

The gaseous epoxidation effluent typically contains from about 0.5 to about 10 mole percent epoxybutene and preferably from about 1 mole percent to about 7 mole percent, about 4 to 50 mole percent butadiene, and about 25 to 85 mole percent reaction diluent gas, e.g., nitrogen, carbon dioxide, methane, ethane, propane, n-butane, or other species inert under reaction. As noted above, the diluent gas, for the purpose of the present invention, preferably is carbon dioxide, nitrogen, ethane, or most preferably, methane. The effluent also contains a total of about 0.5 to 10 mole percent of other constituents such as, water, acrolein, furan, vinylacetaldehyde, and crotonaldehyde, formed in the epoxidation reactor. Unconsumed organic halide also is present in the epoxidation effluent. The hot epoxidation effluent, typically 170 to 270° C., more typically 200 to 250° C., normally is cooled in a heat exchanger by indirect contact with a suitable cooling media such as water, chilled brine, glycol, or cool reactor feed gas, to a temperature of less than 150° C., preferably less than 100° C.

The absorption zone comprises a columnar, pressure vessel containing trays or a packing material that facilitates intimate gas/liquid contact. The absorption vessel normally is provided with means, such as a disengaging space above the packing, to prevent or minimize entrainment of liquids in the gas stream removed from the upper section thereof. The pressurized, cooled, substantially gaseous, epoxidation effluent is fed to the lower section of the absorption vessel, preferably near the bottom of the vessel. A liquid, water-miscible absorbent is fed to the upper section, preferably near the top, of the absorption vessel and flows downward, thereby absorbing or scrubbing the epoxybutene component from the upwardly-flowing epoxidation effluent. A solution of epoxybutene in the absorbent is removed from the base of the absorption vessel and a vapor comprising butadiene, inert diluent, oxygen and carbon dioxide components of the epoxidation effluent is removed from the top of the vessel.

The liquid, water-miscible absorbent is selected from diols, aliphatic and cyclic ethers, alkoxyalkanols, alkanoate esters of alkoxyalkanols, dialkoxyalkanes, alkylnitriles, N,N-dialkylformamides, N,N-dialkylacetamides, N-alkylpyrrolidinones, dialkyl sulfoxides, morpholine, pyridine, or a mixture of any 2 or more thereof and the absorbent compound(s) contain 3 to about 8 carbon atoms. The desirable properties of an absorbent useful in the present invention include: (1) high affinity and capacity for epoxybutene absorption; (2) low specific heat; (3) low of reactivity with epoxybutene and by-products; (4) oxidative stability under absorption and distillation conditions; (5) higher boiling point, e.g., a boiling point of at least about 100° C., preferably at least about 125° C., to reduce losses in absorber off-gas; (6) miscibility with water to allow easy recovery from the absorber off-gas; (7) is a liquid at the normal operating conditions of the recovery process; (8) does not form an azeotrope with epoxybutene or is easily separable from epoxybutene. Although no chemical species possesses all of these desirable characteristics, after extensive testing of candidate absorption solvents, we have found that the classes of compounds set forth above are exemplary solvents for the present invention.

As used herein, the terms "absorbent" and "solvent" are used interchangeably for describing a material or composition that preferentially absorbs epoxybutene from a stream composed of the epoxybutene and other constituents. As used herein, "absorption zone" and "absorber" are used interchangeably as one skilled in the art will recognize that each performs a substantially similar function and accordingly, will be referred to herein as "absorber". As used herein to describe the absorbents, "water-miscible" refers to liquid absorbent compounds which the absorbent-water binary system does not exhibit liquid-liquid phase formation at the absorption and distillation conditions of this invention. Additionally said absorbent compounds have a normal a boiling point of at least about 100° C., preferably at least about 125° C.

Specific examples of suitable solvents include, but are not limited to, 1-methyl-2-pyrrolidinone (NMP), pyridine, 3-butene-1,2-diol (1,2-diol), propylene glycol, dimethylformamide, dimethylacetamide, diethylformamide, diethylacetamide, acetonitrile, dimethylsulphoxide, morpholine, diethylene glycol dimethyl ether, triethylene glycol dimethyl ether, tetraethylene glycol dimethyl ether, propylene glycol monomethyl ether acetate, ethylene glycol monoethyl ether, ethylene glycol monobutyl ether, ethylene glycol monopropyl ether, propylene glycol monomethyl ether, propylene glycol monoethyl ether, propylene glycol monopropyl ether, diethylene glycol monomethyl ether, diethylene glycol monoethyl ether, diethylene glycol monopropyl ether, diethylene glycol monobutyl ether. The preferred water-miscible solvents are 3-butene-1,2-diol and NMP.

The absorber and its contents typically are operated at a temperature between about 0 and 100° C. and at a pressure of about 1 to 17 bara, preferably at a temperature from about 5 to 60° C. and pressure of about 2.5 to about 7.5 bara. The amount of liquid absorbent fed to the absorber can vary substantially depending, for example, on the particular vessel configuration, the use of packing material and its type, and the feed rate and composition of the epoxidation effluent. Generally, the molar ratio of the absorbent feed to the total epoxidation effluent feed via line 1 is in the range of about 15:1 to about 1:20, more typically about 3:1 to 1:5. The temperature of the liquid absorbent feed is in the range of about 0 to 100° C., more preferably about 20 to 70° C.

The effluents from the absorption zone comprise (1) a gaseous effluent comprising butadiene, oxygen and an inert diluent which exits the upper section or top of the absorption vessel and (2) a liquid effluent comprising epoxybutene, the absorbent and water which exits the lower section or bottom of the absorption vessel. The amount of epoxybutene present in the gaseous effluent depends on the absorbent flow rate and the number of stages in the absorber but typically is less than 0.1 weight percent, preferably less than about 0.05 weight percent, and more preferably less than about 250 ppm. The gaseous effluent stream may be recycled to the epoxidation zone. When a significant amount of the butadiene present in the absorber feed gas is absorbed by the absorbent employed, additional butadiene may be fed to the absorber so that the butadiene concentration in the gaseous effluent is suitable for recycling to the epoxidation zone. Alternatively, any makeup butadiene required may be fed to the recycle stream at a point downstream from the absorber. We have found that low levels, e.g., less than 500 ppmv, of substantially all oxygen-containing and nitrogen-containing species useful as absorbents in the process of the present invention can cause a reversible decrease in the activity of the silver epoxidation catalyst when present in the recycle gas to the epoxidation zone. The detrimental effect is generally proportional to the level of the absorbent contained in the recycle gas. Thus, it is beneficial to maintain the level of the absorbent in the gaseous effluent from the absorption zone to as low a level as practical and economical. The gaseous effluent which is recycled to the epoxidation zone normally should contain less than 250 ppmv, preferably less than 100 ppmv, of the absorbent used in the absorption zone. One method of minimizing the absorbent level in the recycle gaseous effluent is to use an absorbent that is substantially non-volatile, i.e., has a vapor pressure of less than about 0.033 bar at the temperature and pressure conditions at the top of absorber 4. Such substantially non-volatile absorbents typically have normal boiling points in excess of about 210° C. Examples of substantially non-volatile absorbents include diethylene glycol and triethylene glycol. Such a stringent vapor pressure requirement severely and unduly limits the choice of potential solvents to very high-boiling species.

The preferred method of minimizing absorbent content in the recycle gas is to use a water wash step wherein the gaseous effluent is fed to the lower section of a water wash column in order to recover a portion of the vaporized water-miscible absorbent present in the gaseous effluent from the absorber. Water is fed to the upper section of the water wash column and contacts the gaseous absorber effluent countercurrently. The water wash column normally contains a suitable packing material or trays to provide intimate vapor/liquid contacting. In this fashion, the water-miscible absorbent content of the gaseous absorber effluent can be reduced easily to less than 100 ppmv, preferably less than 50 ppmv, more preferably less than 25 ppmv. The absorber and water wash column may be two separate pieces of equipment or they may be combined within a single column shell with the upper section of the column separated from the lower section by any appropriate partitioning device known in the art such as a chimney tray with a total liquid draw-off sump. The absorber and water wash column or the single-column combination thereof, also may include a means, such as a disengaging space above the packing, to prevent or minimize entrainment of liquids in the gas stream removed from the upper column section(s).

A liquid effluent comprising water and absorbed water-miscible absorbent is removed from the lower section or bottom of the water wash column. This liquid effluent may be discarded as waste or subjected to further processing for recovery of the water-miscible solvent, e.g., by distillation, or more preferably fed to the upper section of the absorber. A gaseous or vapor effluent comprising butadiene, oxygen and an inert diluent which exits the upper section or top of the water wash may be further processed to remove carbon dioxide before recycling to an epoxidation reactor. Suitable carbon dioxide removal systems are known to those skilled in the art as exemplified by the carbon dioxide removal zones described in U.S. Pat. Nos. 5,117,012 and 5,312,931. Examples of such carbon dioxide scrubbing systems include contacting the carbon dioxide containing stream with an aqueous alkali metal hydroxide, hot potassium carbonate, or aqueous amines in an absorption process known to those skilled in the art.

The separate water-wash step described above may be omitted and the water-miscible absorbent content of the absorber gaseous effluent may be lowered by washing in a carbon dioxide removal zone positioned downstream from the absorber prior to recycling the gas to the epoxidation zone. Suitable carbon dioxide absorbents, i.e., aqueous hot potassium carbonate, aqueous sodium hydroxide, aqueous monoethanolamine, and the like, used in the carbon dioxide removal zone for treatment of the recycle gas, also are capable of absorbing the water-miscible absorbent from the absorber gaseous effluent in a fashion substantially similar to that of a separate water wash column. However, this embodiment is not preferred as the carbon dioxide absorbent becomes contaminated with the water-miscible absorbent and the recovery of the water-miscible absorbent is unduly complicated by such an arrangement.

The liquid effluent comprising epoxybutene, the absorbent and water which exits the lower section or bottom of the absorption vessel normally contains about 1 to 30 weight percent epoxybutene, more typically about 5 to 20 weight percent epoxybutene. This liquid effluent is conveyed to a first distillation column (absorbent recovery column) where epoxybutene, water, and minor amounts of other materials such as butadiene, dissolved oxygen, nitrogen, carbon dioxide, methane or other inert reaction diluent, are stripped from the water-miscible solvent. The liquid effluent is fed to the mid-section, preferably at least 2 theoretical equilibrium stages from the top, of the first distillation column. The section above the feed tray serves as a rectifying section to keep the absorbent out of the distillate. The preferred number of theoretical equilibrium stages in the first distillation column is 4 to 18 stages, preferably 6 to 12 stages. The temperature at the top stage of the first distillation column normally is from about 60 to 105° C., depending the water content of the overhead vapor distillate. The temperature at the base of the first distillation column normally is from about 100 to 270° C., preferably from about 100 to 185° C. The operating pressure of the first distillation column normally is within the range of about 1 to 4 bars, and preferably from about 1 to 2.3 bars.

A vaporous distillate product is removed from the upper section or top of the first distillation column and cooled to condense and separate a liquid product comprising epoxybutene and water from an uncondensed vapor comprising normally gaseous and low boiling components such as oxygen, nitrogen, carbon dioxide, methane or other inert reaction diluent, and butadiene. The liquid product, which typically comprises about 9 to 70 weight percent water and 30 to 91 weight percent epoxybutene, is fed to a decanter wherein the liquid is allowed to settle and separate into two phases. The upper organic phase typically comprises about 90 to 98 weight percent epoxybutene, about 2 to 3 weight percent water, and a trace amount of butadiene. The lower aqueous phase typically comprises about 95 to 97 weight percent water and about 3 to 5 weight percent epoxybutene.

The butadiene and epoxybutene present in the uncondensed vapor from the first distillation column may be recovered by contacting the uncondensed vapor with cooling media at temperatures less than about −10° C. in a heat exchanger. Another method is by vapor recompression followed by heat exchange with a typical cooling media such as cooling water, chilled brine, or glycol. A third and preferred method is absorption in a counter-current absorption tower using the same water miscible absorbent as is used in the absorption zone. The absorbent-containing, recovered butadiene and epoxybutene may be conveyed to the absorption zone for further processing while the gases not dissolved by the absorbent may be vented. This method is preferred when a solvent with high affinity for butadiene is used as the absorbent in the absorption zone. Examples of useful solvents for butadiene recovery in the epoxybutene recovery zone are acetonitrile, NMP, morpholine, dimethylformamide, dimethylacetamide, and other water-miscible, polar, aprotic solvents.

A liquid product comprising water-miscible absorbent, water, and epoxybutene-water reaction products, i.e., 1-butene-3,4-diol, 2 butene-1,4-diol, and higher epoxybutene-derived ether alcohols is removed from the lower section or base of the first distillation column and recycled to the absorption vessel. A portion of the underflow from the first distillation column may be passed through a heat exchanger and returned to the bottom section of the column to provide the heat to operate the first distillation column.

The organic phase from the decanter is fed to the upper section of a second distillation column (epoxybutene purification column) wherein water and any remaining butadiene are stripped from the epoxybutene. The organic phase is fed near the top, e.g., within about three theoretical equilibrium stages from the top, of the second distillation column. The preferred number of theoretical equilibrium stages in the second distillation column is 4 to 20 stages, preferably 6 to 15 stages. The conditions employed within the second distillation column can vary depending on the particular apparatus employed. The temperature at the top stage of the column normally is from about 60 to 75° C., depending the water content of the overhead vapor. The temperature at the base of the second distillation column normally is from about 67 to 120° C., preferably from about 67 to 100° C. The operating pressure of the second distillation column is normally within the range of about 1 to about 4 bara, and preferably from about 1 to about 2.3 bara. A vaporous distillate product exits the top of the second distillation column and is cooled. The composition of vapor product typically is on the epoxybutene-rich side of the epoxybutene-water minimum-boiling azeotrope, and typically comprises about 1 to 8 weight percent water and greater than about 90 weight percent epoxybutene. After cooling, the vapor product is separated into a liquid comprising epoxybutene and water and a vapor comprising uncondensed components such as oxygen, nitrogen, carbon dioxide, methane or other reaction diluent, and saturated with butadiene, epoxybutene, and water. Butadiene and epoxybutene may be recovered from the uncondensed stream by the same means employed for the uncondensed components from the first distillation column. The condensed liquid comprising epoxybutene and water is fed to a decanter such as the decanter referred to above.

A liquid product is removed from the bottom of the second distillation column. Conditions within the second distillation column are adjusted to provide for the recovery of a dehydrated epoxybutene product comprising less than 0.1 weight percent, preferably less than 500 ppm by mass, more preferably less than 150 ppm by mass, water, from the bottom of the second distillation column. Epoxybutene product optionally may be withdrawn as a vapor or liquid from the mid-section of the second distillation column. When epoxybutene product is withdrawn as a sidedraw from the mid-section of the second distillation column, the liquid stream removed from the bottom of the column contains higher boiling epoxybutene oligomers, and 3-butene-1,2-diol by-products. It is possible to achieve epoxybutene product purities of greater than 99 weight percent, preferably greater than 99.5 weight percent, from either the base or mid-section of the second distillation column.

In an optional embodiment or feature of the present invention, the lower aqueous phase which forms in the aforesaid decanter may be fed to the upper section, e.g., within about three theoretical equilibrium stages from the top, of a third distillation column (water column) wherein epoxybutene is stripped from water. The number of theoretical equilibrium stages in the water column typically is 3 to 12 stages, preferably 6 to 10 stages. The temperature at the top stage of the column is normally from about 60 to 105° C., depending the water content of the overhead vapor. The temperature at the base of the water column, e.g., typically provided by a reboiler, normally is from about 100 to 150° C., preferably from about 100 to 120° C. The operating pressure of the third distillation column normally is within the range of about 1 to about 4 bars, and preferably from about 1 to about 2.3 bars.

A vaporous distillate product is removed from the top of the water column and is cooled. The liquid comprising epoxubutene and water condensed from the overhead vapors is returned to the decanter for separation into two phases. The composition of the condensed liquid typically is on the water-rich side of the epoxybutene-water minimum-boiling azeotrope, and typically comprises about 10 to 99 weight percent water and 1 to 90 weight percent epoxybutene, more typically about 15 to 50 weight percent water and 50 to 85 weight percent epoxybutene. A liquid product comprising primarily water is removed from the bottom or base of the water column. The conditions within the water column are adjusted so that the liquid water stream removed from the bottom of the water column comprises less than 0.1 weight percent, preferably less than 500 ppm by mass, more preferably less than 100 ppm by mass of epoxybutene.

The absorbers and distillation columns utilized in the process of this invention typically comprise columnar, pressure vessels containing trays or a packing material that facilitates intimate gas/liquid contact. The gas/liquid contacting equipment in the columns may include, but is not limited to, cross-flow sieve, valve, or bubble cap trays, structured packings such as packings available under the tradenames Mellapak®, Flexipac®, Gempak®, Goodloe®, and Sulzer®, or random or dumped packing, such as berl saddles, Intalox® saddles, raschig rings, Palle rings, and Nutter Rings™. These and other types of suitable gas/liquid contacting equipment are described in detail in Kister, H. Z. Distillation Design, McGraw-Hill, N.Y. (1992), Chapters 6 and 8.

To prevent the formation of butadiene polymerization products in the epoxybutene absorber and/or first distillation column utilized in the operation of the present process, the epoxybutene absorber and first distillation column may be operated in the presence of a polymerization inhibitor known to those skilled in the art. For example, suitable polymerization inhibitors include tertiary butyl catechol or amine oxide compounds. The polymerization inhibitor may be added to the upper section of the epoxybutene absorber and first distillation column. The formation of low molecular weight, butadiene polymerization products are substantially suppressed by the addition of about 300 to 400 ppm Actrene 230 inhibitor, based on the amount of vapor removed from the column. The inhibitor addition point can be any place that is convenient for the operation of the first distillation column by means of a low-flow addition device such as a syringe pump.

Epoxybutene reacts readily with nucleophiles such as water and alcohols to form 3-butene-1,2-diol and glycol ethers, respectively. However, the relative rate of epoxybutene reaction with nucleophiles is a function of pH. Epoxybutene, like other epoxides, undergoes both acid and base catalysis. Acid catalysis has the larger influence on the rate of reaction. For example, the rate of epoxybutene hydrolysis in over 500 times greater at pH 3 than at pH 7. At pH 11, the rate is over 17 times greater than at pH 7. At pH 8, the rate is only about 0.7 times that at pH 7. Since it is desirable to minimize epoxybutene losses due to reaction with nucleophiles, epoxybutene reactivity can be reduced by maintaining epoxybutene-laden solutions at or near a pH of about 6 to 9. This can be done by adding a base compound to the recovery system. See, for example, the procedures described in U.S. Pat. No. 5,756,779. Thus, any basic material that is capable of neutralizing organic acids may be used in the present process. Examples include Group Ia (alkali) metal hydroxides, bicarbonates, carbonates, and phosphates; Group IIa (alkali earth) metal hydroxides and carbonates; ammonia; ammonium hydroxide, bicarbonate, carbonate, and phosphate; amines such as tertiary amines, e.g., trialkyl amines containing up to about 18 carbon atoms; amino alcohols, such as tertiary aminoalkanols, e.g., N,N-dialkylaminoalkanols containing up to about 20 carbon atoms; basic ion-exchange resins, and similar materials. The base compound should be stable, or substantially stable, under the distillation conditions employed in the process. The use of phosphate buffers, ammonia, ammonium buffers, and/or alkyl amines are the preferred methods.

The base component or components may be added to the absorption/distillation system as an aqueous mixture on an as needed basis to maintain the pH with the proper range. The base solution may be added to any or all of the following locations including the absorption column, the first distillation column (solvent recovery column), the water-wash column, the decanter of the first distillation column, and the third distillation. It is not preferable to add the base solution to the second epoxybutene drying column because many of the favored base components are not soluble in epoxybutene in the absence of water.

Referring to the accompanying Figure, cooled reaction effluent is fed via line 1 to the lower section of absorber 2 and water-miscible absorbent is fed via line 3 to the upper section of the absorber, preferably near the top. The absorbent flows downward countercurrent to the rising gaseous epoxidation effluent and absorbs epoxybutene from the gaseous effluent. A gaseous effluent comprising butadiene, oxygen, inert diluent and minor amounts of other compounds exits the upper section or top of the absorber 2 through line 5. The gaseous effluent may be recycled via lines 5, 6 and 7 to the butadiene epoxidation zone after some or all of the effluent has been treated, for example in a carbon dioxide removal zone. Alternatively, the gaseous effluent may be transported via lines 5 and 8 to the lower section or bottom of water wash vessel or column 10 wherein the gaseous effluent in contacted with water which is fed to the upper section or top of column 10 through conduit 11. The descending water absorbs all or essentially all of any water-miscible absorbent present in the gas fed via line 8. The water containing the water-miscible absorbent is removed from the lower section or bottom of water wash vessel 10 through line 12. The water/absorbent liquid may be discarded from the recovery system through lines 12 and 13 or transported to means (not shown), e.g., a distillation column, for recovery of the absorbent. Preferably, the water/absorbent liquid is transferred via lines 12 and 14 to the upper section or top of absorber 2. A gaseous effluent is removed from water wash column 10 via line 15 and recycled by means of line 7 to the epoxybutene production system. To moderate the temperature within absorber 2, liquid may be removed via line 15, passed through heat exchanger 16 wherein the temperature of the liquid is lowered, and returned to the absorber through line 17.

Epoxybutene-rich absorbent is removed from the lower section or bottom of absorber 2 and conveyed via line 19 to the mid-section of first distillation column 20 wherein epoxybutene, water, butadiene and other low boiling materials are separated from the water-miscible absorbent. Additional water may be added to the bottom-section of the column 20 via conduit 33 to ensure adequate water concentration in the stripper feed to remove azeotropically all of the absorbed epoxybutene as the epoxybutene/water azeotrope without providing external reflux. The epoxybutene-rich absorbent is fed to the mid-section of column 20 and a vaporous product is removed from the column by line 21 and partially condensed in heat exchanger 22. Non-condensed components comprising oxygen, nitrogen, carbon dioxide, methane and/or other process diluent and saturated with butadiene, epoxybutene and water are removed through line 23 and may be treated further as described above to recover the butadiene and epoxybutene components from the non-condensed stream.

Condensed liquids comprising epoxybutene and water are conveyed via conduit 24 to reflux decanter tank 40 wherein the condensed distillate, typically comprising about 9 to 70 weight percent water and 30 to 91 weight percent epoxybutene, is allowed to settle and separate into two phases. The upper, organic phase typically comprises 90 to 98 weight percent epoxybutene, about 2 to 3 weight percent water and butadiene. The lower, aqueous phase typically comprises about 95 to 97 weight percent water and 3 to 5 weight percent epoxybutene. Reflux is provided to column 20 by line 25. The reflux may be a fraction of the upper phase, a fraction of the lower phase or a mixed fraction of the upper and lower phases.

A liquid comprising water-miscible absorbent or solvent, water, and epoxybutene-water reaction products, i.e., 1-butene-3,4-diol, 2 butene-1,4-diol, and higher epoxybutene-derived ether alcohols is removed from the base of column through line 26 and recycled to absorber 2 via line 27, heat exchanger 28, and line 3. Heat exchanger 28 may be utilized to adjust the temperature of the recycle liquid of line 27 to that desired for the absorbent fed to column 2, e.g., from about 0 to 100° C., preferably from about 20 to 70° C. Stream 19 may be heat-interchanged with stream 27 to improve the energy efficiency of the process. Fresh, make-up absorbent may be added to the recovery system by means of line 29.

A portion of column underflow 26 may be diverted through line 30, heat exchanger 31, and line 32 to provide the heat (boilup) required for the operation of absorbent recovery column 20. Some or all of the required heat may be provided in the form of steam or hot water fed to the base of column 20 to steam strip epoxybutene from the recyclable bottoms absorbent product removed through line 26.

The epoxybutene-rich, upper, liquid phase contained in decanter 40 is conveyed via line 41 to a second distillation column (epoxybutene purification column) at a point near the top of column 41, e.g., within about three theoretical equilibrium stages from the top. A vaporous distillate product is removed from the top of column 42 through line 43 and fed to partial condenser 44 wherein a portion of the distillate is condensed. The condensed liquids comprising epoxybutene and water are conveyed from partial condenser 44 by line 45 to decanter 40. The uncondensed components, e.g., oxygen, nitrogen, carbon dioxide, methane and/or other process diluent, saturated with butadiene, epoxybutene and water are removed through line 46 and normally are treated to recover the butadiene and epoxybutene present therein. The uncondensed stream of line 46 may be treated with and in the same manner as uncondensed stream 23 is treated for recovery of butadiene and epoxybutene. Condenser 22 and condenser 44 serve essentially the same function and, to conserve capital expense, may be physically the same piece of equipment.

Liquid, dehydrated, epoxybutene product is removed from the lower section or base of column 42 through line 47 and normally constitutes the final, purified epoxybutene product of the epoxybutene recovery and purification process described herein. By proper control of temperatures, pressures and boilup rate within column 42, the epoxybutene underflow product contains less than 0.1 weight percent, preferably less than 500 parts per million by weight (ppmw), and most preferably less than 150 ppmw, water. A portion of underflow stream 47 is diverted by means of line 48, heated in heat exchanger 49 and fed via line 50 to the lower section near the bottom of column 42 to provide the heat required for the operation of the column. If the epoxybutene product stream is withdrawn from column 42 via line 47, then said product will contain in addition to epoxbutene, higher boiling components such as epoxybutene oligomers and 3-butene-1,2-diol by-products formed in column 42 or introduced into column 42 via feed line 41.

Alternatively and preferably, liquid, dehydrated, epoxybutene product may be withdrawn as a vapor or liquid via line 51 from the side of column 42 (column sidedraw), preferably at least one theoretical stage above the feed of reboiler feed line 50. If stream 51 is withdrawn as a vapor, the product is condensed in condenser 52 and recovered as a liquid through line 53. When stream 51 is withdrawn as a liquid, condenser 52 can be used to cool the product. Epoxybutene product is withdrawn as sidedraw steam 51, stream 47 removed from the base of column 42 comprises epoxybutene containing higher boiling components such as epoxybutene oligomers and 3-butene-1,2-diol by-products.

In accordance with the process of the present invention, it is possible to obtain epoxybutene of greater than 99 weight percent purity, preferably greater than 99.5 weight percent purity, from either line 47 or 53. The lower aqueous phase contained in decanter 40 may be fed to the upper section, e.g., within about three theoretical equilibrium stages from the top, of third distillation column (water column) 60 via conduit 61. The purpose of water column 60 is to strip epoxybutene from the aqueous phase from the decanter. A vaporous distillate product is removed from the top of the water column through line 62, cooled in condenser 65 to condense the distillate vapor, and the resulting liquid is conveyed by means of line 64 to decanter 40 for separation into two phases. The composition of the condensed liquid typically is on the water-rich side of the epoxybutene-water minimum-boiling azeotrope, and typically comprises about 10 to 99 weight percent water and 1 to 90 weight percent epoxybutene, more typically about 15 to 50 weight percent water and 50 to 85 weight percent epoxybutene. A liquid product comprising primarily water is removed via line 65 from the bottom or base of water column 60. Water column 60 is operated in a manner so that the liquid water stream removed via line 65 comprises less than 0.1 weight percent, preferably less than 500 ppm by weight, more preferably less than 100 ppm by weight, epoxybutene. A portion of underflow stream 65 is diverted by means of line 66, heated in heat exchanger 67 and fed via line 68 to the lower section near the bottom of column 60 to provide the heat required for the operation of the column.

EXAMPLES

The recovery and purification process provided by the present invention is further illustrated by the following examples. The percentages specified in the examples are by weight unless otherwise specified.

Example 1

This example illustrates the efficacy of a continuously recycled absorbent comprising NMP and water for epoxybutene absorption from the product gas of an epoxidation reaction zone. The embodiment of this process as practiced in this example is shown in the Figure. After partial removal of carbon dioxide, the gaseous effluent from absorber 2 passed through an epoxidation zone comprising two identical stainless steel tubes, 7.62 meters tall, 18.7 mm inside diameter, packed with 1.2 meters of Denstone ceramic packing on top of 3 meters of silver/cesium/alumina catalyst rings. The epoxidation zone was maintained at an average maximum temperature of about 240° C. at an inlet pressure of about 5.25 bara (76 psia).

The epoxidation catalyst employed comprised an alumina support in the form of 6 mm outside diameter rings having deposited thereon 12% silver and 700 ppmw cesium. The catalyst was prepared according to known procedures, e.g., as exemplified by U.S. Pat. No. 4,897,498, by impregnating the support material with solutions of a silver amine salt and cesium chloride followed by a thermal decomposition/reduction treatment in the presence of an oxygen-containing gas to convert the silver salt to silver metal.

The epoxybutene-laden reactor product gas, at an average rate of 140 to 300 standard liters per minute, with average composition comprising about 12 mole percent oxygen, 12 mole percent 1,3-butadiene, 63 mole percent methane, 2–4 ppmv ethylchloride, 20 ppm trimethylamine, 4 mole percent carbon dioxide, and 5 mole percent nitrogen and argon was cooled to about 34° C. This gas was fed via line 1 to the lower section of epoxybutene absorber 2 comprising a stainless steel column, 83 mm inside diameter, packed with about 1.8 meters of 9.5 mm stainless steel Penn State packing. A recycle absorbent mixture comprising on average 93% NMP, 1% 1,2-diol, 1% oligomers, and 5% water was fed at a rate of about 11 liters per hour to the upper section of the absorber via conduit 3. The absorbent feed temperature was maintained at about 29° C. by heat exchanger 28 by indirect contact with cooling water. The absorber operated at an outlet pressure about 4.5 bara, with an average temperature of about 30° C. The epoxybutene concentration in the vapor removed through line 5 was below detection limits. Approximately 60% of the butadiene in the epoxidation effluent gas contained in conduit 1 was absorbed along with the epoxybutene. To maintain the proper butadiene concentration in the off-gas removed by line 5, fresh butadiene was added via line 4 at a rate of about 1000 g/hour to absorber 2. Absorption of trimethylamine from the reactor product effluent was sufficient to maintain the epoxybutene-rich absorbent pH at a value of about 8 to 9.

The epoxybutene-rich absorber solution was removed through line 19, preheated to a temperature of 95° C., and fed at a rate of about 11 liters per hour to the middle of solvent distillation column 20 comprising a stainless steel column, 71 mm in diameter, packed with about 1.5 meters of 9.5 mm stainless steel Penn State packing. The bottom of the column contained a 6 mm diameter stainless steel heating coil, reboiler 31. Heat was supplied by condensation of 4.6 bar (67 psig) steam in the heating coil of heat exchanger 31. Additional distilled, demineralized water was added to the lower section of the column via conduit 33 at a rate of 1.6 liter/hour to ensure adequate water concentration in the stripper feed to remove azeotropically all of the absorbed epoxybutene as the epoxybutene/water azeotrope without providing external reflux. The base temperature of the solvent distillation 20 was maintained at about 150° C., while the top temperature was about 77° C. A vapor was removed via line 21 and was partially condensed against cooling water at a temperature of 20° C. in heat exchanger 22. Condensed stream 24 comprising epoxybutene, water, and butadiene was collected and removed from the system. Stream 23 comprising noncondensable gases such as carbon dioxide, oxygen, nitrogen, argon, and saturated with water, EpB, and butadiene vapors was expelled from the system. NMP extractent was washed out of the absorber vapor effluent stream 5 by contacting it with aqueous monoethanolamine in a carbon dioxide removal zone prior to recycle to the epoxidation reactor.

Example 2

This example illustrates the efficacy of a continuously recycled absorbent comprising 1,2-diol and water for epoxybutene absorption from the product gas of an epoxidation reaction zone. The embodiment of this process as practiced in this example is in the Figure. The reactor system described for Example 1 was used for Example 2.

An epoxybutene-laden reactor product gas 1 was cooled to about 34° C. and fed at an average rate of 140 to 300 standard liters per minute to the lower section of epoxybutene absorber 2. Absorber 2 consisted of a stainless steel column, 83 mm inside diameter, packed with about 1.8 meters of 9.5 mm stainless steel Penn State packing. The average composition of the reactor product gas was about 12 mole percent oxygen, 12 mole percent 1,3-butadiene, 63 mole percent methane, 2–4 parts per million by volume (ppmv) ethylchloride, 20 ppmv trimethylamine, 4 mole percent carbon dioxide, and 5 mole percent nitrogen and argon. A recycled absorbent mixture comprising on average 85 weight percent 1,2-diol, 5 weight percent oligomers, and 10 weight percent water was fed at a rate of about 14 liters per hour to the upper section of absorber 2 via conduit 3. The absorbent feed temperature was maintained at about 29° C. by heat exchanger 28 by indirect contact with cooling water. Absorber 2 was operated at an outlet pressure about 4.5 bara and average temperature of about 30° C. The epoxybutene concentration in the off-gas of line 5 averaged about 200 to 500 ppm. Approximately 35% of the butadiene in the reactor product gas fed to the absorber was absorbed along with the epoxybutene. To maintain a butadiene concentration in the off-gas of line 5 suitable for recycling to the epoxidation reaction zone, fresh butadiene was added at a rate of about 700 g/hour to EpB absorber 2 via line 4. Absorption of trimethylamine from the reactor product effluent was sufficient to maintain the epoxybutene/absorbent of line 19 at a pH of about 8 to 9.

The epoxybutene/absorber solution of line 19 was preheated to a temperature of 90° C. and fed at a rate of about 14 liters per hour to the middle of absorbent recovery column 20 comprising a stainless steel column, 71 mm in diameter, packed with about 1.5 meters of 9.5 mm stainless steel Penn State packing. The bottom of the column contained a 6 mm diameter stainless steel heating coil, reboiler 31. Heat was supplied by condensation of 2.6 bar (38 psig) steam in the heating coil. The base temperature of the absorbent column 20 was maintained at about 130° C., while the top temperature was about 80° C. The overhead vapor was partially condensed against cooling water at a temperature of 20° C. in heat exchanger 22. Stream 26 comprising epoxybutene, water, and butadiene was collected and removed from the system. Stream 23 comprising noncondensable gases such as carbon dioxide, oxygen, nitrogen, argon, and saturated with water, epoxybutene, and butadiene vapors was expelled from the system. Absorbent was washed out of the absorber vapor effluent of line 5 by contacting the effluent with aqueous monoethanolamine in a carbon dioxide removal zone prior to recycle to the epoxidation reactor.

Example 3

This example compares the absorption affinity of various water-miscible solvents for epoxybutene in the presence of water, as occurs in the absorbent zone of the present invention. A standard mixture of 2 parts by weight water and one part by weight epoxybutene was prepared. A portion of the standard solution was placed in a separatory funnel, shaken, allowed to settle, then separated into two liquid phases at room temperature. The water phase was analyzed by gas chromatography to determine the solubility of epoxybutene in pure water. Next, for each solvent specified in Table I, one part by weight water-miscible solvent was added to two parts of the standard water-epoxybutene solution. Each water-solvent-epoxybutene solution was placed in a separatory funnel, shaken, allowed to settle, then separated into two liquid phases at room temperature. The aqueous phase from the decantation was analyzed by gas chromatography to determine the epoxybutene solubility in that phase. From these compositions, distribution coefficients were calculated as:

$$\text{Distribution coefficient} = \frac{\text{Moles epoxybutene in organic layer}}{\text{Moles epoxybutene in aqueous layer}}$$

The relative affinity of solvents for absorption of epoxybutene was determined from a relative molar distribution term, calculated as:

$$\text{Relative distribution} = \frac{\text{Distribution coefficient in presence of solvent}}{\text{Distribution coefficient in water only system}}$$

A relative distribution coefficient greater than unity indicates that the solubility of epoxybutene in the aqueous layer has increased in the presence of the solvent. A solvent with a relative distribution coefficient greater than unity has a greater affinity for epoxybutene compared to water alone, and thus is a better solvent for epoxybutene than water. Results are given in Table I.

TABLE I

| Water-Miscible Absorbent | Relative Distribution |
| --- | --- |
| 1-Methyl-2-Pyrrolidinone | 2.78 |
| Ethylene Glycol | 1.14 |
| Propylene Glycol | 1.90 |
| 3-Buten-1,2-Diol | 1.39 |
| Dimethylformamide | 2.44 |
| Dimethylacetamide | 2.68 |
| Acetonitrile | 1.89 |
| Dimethylsulfoxide | 1.40 |
| 2-Methoxypropyl Acetate | 1.05 |
| 2-(2-Butoxyethoxy)ethanol | 4.30 |
| 2-(2-Methoxyethoxy)ethanol | 1.83 |
| 2-Butoxyethanol | 1.29 |
| 2-Propoxyethanol | 1.49 |
| Propylene Glycol Monomethyl Ether | 2.02 |
| Quinoline | 1.03 |
| Triglyme | 1.54 |
| No solvent (100% Water) | 1.00 |

Example 4

The rate of epoxybutene hydrolysis was determined at several different pH levels according to the following procedure: A stirred, thermostatted cell was filled with a solution of buffered water and allowed to equilibrate at a temperature of 29° C. Phosphate buffers at a pH of 3, 5, 7, 8, 9, and 11 were prepared by adding either phosphoric acid or sodium hydroxide to a 0.05 M solution of disodium phosphate. For each experiment, the buffer solution was charged to a stirred, thermostatted equilibrium cell equipped with an UV spectrophometer probe. Once the solution had equilibrated at 29° C. and a background spectra had been collected, a 10 microliter standard sample of epoxybutene in acetonitrile (warmed to 29° C.) was injected into the cell to give an initial concentration of 0.01M epoxybutene. The disappearance of epoxybutene and formation of 3-butene-1,2-diol over time was followed by UV spectrophotometry.

The relative rate of epoxybutene hydrolysis as a function of pH is presented in Table II. This data clearly shows that the rate of epoxybutene hydrolysis can be reduced by maintaining the epoxybutene-laden solution at or near a pH of about 7 to 8.

TABLE II

| Solution pH | Relative Rate of Epoxybutene Hydrolysis |
| --- | --- |
| 3 | 555.5 |
| 5 | 5.6 |
| 7 | 1.0 |
| 8 | 0.7 |
| 9 | 3.2 |
| 11 | 17.6 |

Examples 5–9 and Comparative Examples 1–2

Mixtures comprising water, epoxybutene, and water-miscible absorbent were distilled continuously to demonstrate the recovery of epoxy-butene from such absorbents as an epoxybutene-water distillate mixture. Examples 5–8 and Comparative Examples 1–2 were conducted in a distillation system consisting of a silvered, vacuum-jacketed glass Oldershaw column, equipped with a liquid-dividing distillation head, feed tray, reflux magnet, reflux timer, cooling water condenser, jacketed reboiler, pressure gage, and nitrogen purge line. The column was configured with a 15-plate stripping section, a 10-plate rectifying section, and a 500 ml jacketed flask heated by a thermostatted circulating oil bath. A liquid absorber effluent was supplied from a 5-liter jacketed vessel via a piston pump and fed to the middle section of the column. A liquid was removed from the bottom of the column (bottoms take-off) via a second piston pump. The liquid bottoms product was cooled in a small water-chilled, stainless steel heat exchanger placed in line on the suction side of the pump. Condensed vapors from the top of the column was condensed in a cooling water condenser and was conveyed via the liquid-dividing head either to the column as reflux or as take-off as determined by the reflux timer and desired reflux ratio. The take-off stream flowed by gravity to a jacketed cooled receiver, which also functioned as a phase decanter. Thermocouples were provided at the reboiler and distillation head. The duration of each continuous run was from eight to 14 hours. For all examples a reflux ratio of 1:1 was employed. Feed compositions and conditions for each example are given in Tables 2 and 4. In all examples the distillate separated into two phases upon standing. This two-phase mixture was decanted and stored separately as water-rich and epoxybutene layers for feed to subsequent distillation steps.

Distillate and bottoms temperatures, system pressure, and measured pH of the feed and bottoms products are given in Tables 3 and 5. All sampled were analyzed by gas chromatography using a thermal conductivity detector. Mass balances were done to determine percent distillate, distillate and bottoms compositions, percent epoxybutene loss, the recovery of unreacted epoxybutene, and rate of oligomer formation. These results are presented in Tables 3 and 5 wherein "EpB" is 3,4-epoxy-1-butene, "1,2-diol" is 3-butene-1,2-diol, "NMP" is 1-methyl-2-pyrrolidinone, and "oligomer" is the successive reaction products of one or more molecules of EpB with itself or 1,2-diol. The following terms used in Tables 3 to 5 are defined herein as follows.

$$\text{Percent Distillate} = \frac{\text{Mass of Distillate Collected}}{\text{Mass of Material Fed to Column}} \times 100$$

$$\text{Percent Epoxybutene Loss} = \frac{\text{Mass Epoxybutene in Distillate} + \text{Mass Epoxybutene Collected in Bottoms}}{\text{Mass of Epoxybutene Fed to Column}}$$

$$\text{Recovery of Unreacted } EpB = \frac{\text{Mass } EpB \text{ in Distillate}}{\text{Mass Epoxybutene in Distillate} + \text{Mass Epoxybutene in Bottoms}}$$

$$\text{Oligomer Make-rate} = \frac{\text{Mass Oligomer in Distillate and Bottoms}}{\text{Mass of Epoxybutene Lost}}$$

Comparative Example 1

This example illustrates operation of the solvent recovery (first) distillation when the pH in the column is outside of the scope of this invention. A liquid absorber effluent having a pH of 5 and comprising 45.4% water, 45.5% 1,2-diol, and 9.1% epoxybutene was fed to the distillation apparatus. A total of 1121.2 g of absorber effluent was fed. During the distillation, the temperature at the top of the column was 80.10° C. and 106.0° C. at the bottom of the column. The overall composition of the condensed distillate (percent distillate=2.5%) was 16% water, 84% epoxybutene and <0.01% 1,2-diol. The distillate separated into two phases upon standing. The bottoms liquid product had a pH of 5 and comprised 59.2% water, 39.9% 1,2-diol, 0.14% epoxybutene and 0.14% oligomer. The percentage of unreacted epoxybutene recovered was 93.2% and the oligomer formation rate was 1.4%. The percentage epoxybutene loss was 66%.

Comparative Example 2

This example illustrates operation of the solvent recovery (first) distillation when the pH in the column is outside of the scope of this invention. A liquid absorber effluent comprising 35.5% water, 55.8% 1,2-diol, 8.25% epoxybutene, and 0.022% oligomer was mixed with potassium carbonate/phosphoric acid buffer solution and fed to the distillation apparatus. The pH of the feed mixture was 8. A total of 3910.6 g of absorber effluent was fed. During the distillation, the temperature at the top of the column was 62.9° C. and 107.6° C. at the bottom of the column. The overall composition of the condensed distillate (% distillate=9.66%) was 10.8% water, 89.1% epoxybutene and 0.08% 1,2-diol. The distillate separated into two phases upon standing. The bottoms liquid product comprising 37.0% water, 62.5% 1,2-diol, no detectable epoxybutene and 0.05% oligomer, had a measured pH of 11 due to decomposition of the buffer system. The percentage of unreacted epoxybutene recovered was 100% and the oligomer formation rate was 3.1%. The percentage epoxybutene loss was 5.9%.

Example 5

This example illustrates operation of the solvent recovery (first) distillation when the pH in the column is maintained within the scope of this invention by addition of a buffer solution. A liquid absorber effluent comprising 34.8% water, 56.3% 1,2-diol, 8.6% epoxybutene, and 0.043% oligomer was mixed with potassium carbonate/phosphoric acid buffer solution and fed to the distillation apparatus. The pH of the feed mixture was 8. A total of 3340.1 g of absorber effluent was fed. During the distillation, the temperature at the top of the column was 93.1° C. and 109.7° C. at the bottom of the column. The overall composition of the condensed distillate (% distillate=17.2%) was 51.4% water, 48.5% epoxybutene and 0.08% 1,2-diol. The distillate separated into two phases upon standing. The bottoms liquid product, comprising 29.5% water, 69.9% 1,2-diol, no detectable epoxybutene and 0.09% oligomer had a measured pH of 8. The percentage of unreacted epoxybutene recovered was 100% and the oligomer formation rate was 3.3%. The percentage epoxybutene loss was 2.9%.

Example 6

This example illustrates operation of the solvent recovery (first) distillation when the pH in the column is maintained within the scope of this invention by the inherent pH of the absorbent. A liquid absorber effluent comprising 10.13% water, 80.76% NMP, 9.06% epoxybutene, and 0.05% 1,2-diol was fed to the distillation apparatus. A total of 1199.8 g of absorber effluent was fed. During the distillation, the temperature at the top of the column was 88.7° C. and 163.0° C. at the bottom of the column. The overall composition of the condensed distillate (% distillate=13.6%) was 44.7% water, 55.3% epoxybutene, <0.01% NMP and 0.06% 1,2-diol. The distillate separated into two phases upon standing. The composition of the bottoms liquid product comprising 2.90% water, 96.88% NMP, 0.07% 1,2-diol, 0.14% epoxybutene and no detectable oligomer. In this experiment, no extraneous basic material was added to adjust the pH resulting in the liquid bottoms product having a pH of about 6. The percentage of unreacted epoxybutene recovered was 98.4% and the percentage epoxybutene loss was 0.27%. No oligomer formation was detected.

Example 7

This example illustrates operation of the solvent recovery (first) distillation when the pH in the column is maintained within the scope of this invention by the inherent pH of the absorbent. The epoxybutene-free water/NMP liquid bottoms product resulting from the distillation carried out in Example 6 was saturated with fresh epoxybutene and again distilled. The composition of the feed was 9.99% water, 80.69% NMP, 9.3% epoxybutene, and 0.05% 1,2-diol and the material fed was 3206.2 g. During the distillation, the temperature at the top of the column was 91.8° C. and 164.0° C. at the bottom of the column. The overall composition of the condensed distillate (% distillate=15.4%) was 45.2% water, 54.6% epoxybutene, 0.06% NMP and 0.06% 1,2-diol. The distillate separated into two phases upon standing. The composition of the bottoms liquid product comprising 2.36% water, 97.5% NMP, 0.1% 1,2-diol, 0.02% epoxybutene and no detectable oligomer. In this experiment, no extraneous basic material was added to adjust the pH resulting in the liquid bottoms product having a pH of about 6. The percentage of unreacted epoxybutene recovered was 99.8% and the percentage epoxybutene loss was 0.43%. No oligomer formation was detected.

Example 8

This example illustrates operation of the solvent recovery (first) distillation when the pH in the column is maintained within the scope of this invention by the inherent pH of the absorbent. A liquid absorber effluent comprising 4.91% water, 84.99% NMP, 9.3% epoxybutene, and 0.1% 1,2-diol was fed to the distillation apparatus. A total of 3199.2 g of absorber effluent was fed. During the distillation, the temperature at the top of the column was 79–81° C. and 162.5° C. at the bottom of the column. The overall composition of the condensed distillate (% distillate=11.8%) was 24.8% water, 75.1% epoxybutene, <0.001% NMP and <0.01% 1,2-diol. The distillate separated into two phases upon standing. The composition of the bottoms liquid product comprising 3.12% water, 96.7% NMP, 0.16% 1,2-diol, and no detectable epoxybutene or oligomer. In this experiment, no extraneous basic material was added to adjust the pH resulting in the liquid bottoms product having a pH of about 6. The percentage of unreacted epoxybutene recovered was 99.9% and the percentage epoxybutene loss was 0.51%. No oligomer formation was detected.

Examples 9–11

Epoxybutene-rich distillate phases produced in the manner described in Examples 5–8 were distilled to demonstrate recovery of epoxybutene in a distillation system consisting of a silvered, vacuum-jacketed, glass Oldershaw column, equipped with a liquid-dividing distillation head, feed tray, reflux magnet, reflux timer, cooling water condenser, jacketed reboiler, pressure gage, and nitrogen purge line. The column was configured with a 15-plate stripping section, a 10-plate rectifying section, and a 500 ml jacketed flask heated by a thermostatted circulating oil bath. Feed material was supplied from a 5-liter jacketed vessel and fed to the middle section of the column via a piston pump. A liquid column bottoms stream was removed from the base of the column via a second piston pump. Since the feed mixture comprised little water, the pH of the feed mixture was not measured, nor was any buffer solution added.

The liquid bottoms product was cooled in a small, water-chilled, stainless steel heat exchanger placed in line on the suction side of the pump. The distillate product flowed by gravity to a jacketed cooled receiver, which also functioned as a phase decanter. For all examples a reflux ratio of 1:1 was employed. Thermocouples were provided at the reboiler, and distillation head. Each continuous run lasted from eight to 12 hours in duration. In all examples the distillate separated into two phases upon standing. This two-phase mixture was decanted and stored separately as water-rich and epoxybutene phases.

All samples were analyzed by gas chromatography using a thermal conductivity detector. Mass balances were done to determine percent distillate, distillate and bottoms compositions, percent epoxybutene loss, the recovery of unreacted epoxybutene, and oligomer formation rate.

Example 9

This example illustrates operation of the EpB purification (second) distillation column. The epoxybutene-rich feed material comprised 97.9% epoxybutene, 2.1% water, and no detectable 1,2-diol or oligomer. A total of 2600.4 g of material was fed. During the distillation, the temperature within the column was 63.6° C. at the top, 68.6° C. at the bottom, and 65.3° C. at the feed tray. The pressure within the column was 736 torr. The overall composition of the condensed distillate (% distillate=38.16%) was 4.9% water, 94.9% epoxybutene, and no detectable 1,2-diol. The distillate separated into two phases upon standing. The composition of the bottoms liquid product was 99.92% epoxybutene, 0.01% water, 0.04% 1,2-diol, and no detectable oligomer. The epoxybutene loss was 0.02%. No oligomer formation was detected.

Example 10

This example illustrates operation of the EpB purification (second) distillation column. The epoxybutene-rich feed material comprised 98.0% epoxybutene. 2.0% water, 0.01% 1,2-diol, and no detectable oligomer. A total of 2611.0 g of material was fed. During the distillation, the temperature within the column was 62.5° C. at the top, 68.6° C. at the bottom, and 65.8° C. at the feed tray. The pressure within the column was 738 torr. The overall composition of the condensed distillate (% distillate=42.7%) was 5.0% water, 95.0% epoxybutene, and no detectable 1,2-diol. The distillate separated into two phases upon standing. The composition of the bottoms liquid product was 99.84% epoxybutene, 0.02% water, 0.08% 1,2-diol, and no detectable oligomer. The epoxybutene loss was 0.04%. No oligomer formation rate was detected.

Example 11

This example illustrates operation of the EpB purification (second) distillation column. The epoxybutene-rich feed material comprised 97.8% epoxybutene. 2.1% water, 0.08% 1,2-diol, and no detectable oligomer. A total of 4759.3 g of material was fed. During the distillation, the temperature within the column was 64.8° C. at the top, 69.0° C. at the bottom, and 66.2° C. at the feed tray. The pressure within the column was 738 torr. The overall composition of the condensed distillate (% distillate=70.61%) was 2.8% water, 97.0% epoxybutene, and <0.01% 1,2-diol. The distillate separated into two phases upon standing. The composition of the bottoms liquid product was 99.4% epoxybutene, 0.04% water, 0.50% 1,2-diol, and <0.01% oligomer. The epoxybutene loss was 0.052%. The oligomer formation rate was 4.2%.

Example 12

This example illustrates operation of the water removal (third) distillation column. A water-rich distillate phase produced as described in Examples 5–11 was distilled to demonstrate the recovery of epoxybutene from a dilute aqueous solution. The distillation system consisted of a silvered, vacuum-jacketed glass Oldershaw column, equipped with a liquid-dividing distillation head, feed tray, reflux magnet, reflux timer, cooling water condenser, jacketed reboiler, pressure gage, and nitrogen purge line. The column was configured with a 15-plate stripping section, a 10-plate rectifying section, and a 500 ml jacketed flask heated by a thermostatted circulating oil bath. Thermocouples were provided at the reboiler and distillation head. The continuous distillation was carried out over 12 hours. All samples were analyzed by gas chromatography using a thermal conductivity detector. A mass balance was done to determine percent distillate, distillate and bottoms compositions, percent epoxybutene loss, the recovery of unreacted epoxybutene, and oligomer make-rate. A feed material comprising 96.92% water, 3.0% epoxybutene, 0.09% 1,2-diol and no detectable oligomer was supplied from a 5-liter jacketed vessel and fed to the middle section of the column via a piston pump. The pH of the feed mixture was adjusted to a value of 8 by the addition of a $K_2CO_3$—$H_3PO_4$ buffer solution. A total of 2579.1 g of material was fed. During the distillation, the temperature within the column was 96.7° C. at the top, 102.1° C. at the bottom, and 99.3° C. at the feed tray. The pressure within the column was 740 torr. A reflux ratio of 1:1 was employed for this experiment. A distillate product flowed by gravity to a jacketed cooled receiver, which also functioned as a phase decanter. The distillate separated into two phases upon standing. This two-phase mixture was decanted and stored separately as water-rich and epoxubutene-rich phases.

The overall composition of the condensed distillate (% distillate=9.3%) was 23.9% water, 76.0% epoxybutene, and 0.08% 1,2-diol. A liquid bottoms stream comprising 99.9% water, 0.1% 1,2-diol, and no detectable epoxybutene or oligomer was removed from the base of the column via a second piston pump. The bottoms liquid product was cooled in a small water-chilled, stainless steel heat exchanger placed in line on the suction side of the pump. The pH of the liquid bottoms stream was about 9. The recovery of the unreacted epoxybutene was 100% and no oligomer formation was detected. The percentage epoxybutene loss was 2.9%.

The invention has been described in detail with particular reference to preferred embodiments thereof, but it will be understood that variations and modifications can be effected within the spirit and scope of the invention.

We claim:

1. Process for the recovery of epoxybutene from a substantially-gaseous effluent from an epoxidation zone wherein butadiene is contacted with an oxygen-containing gas in the presence of a catalyst and an inert diluent, to produce an epoxidation effluent comprising epoxybutene, butadiene, oxygen, an inert diluent and water which comprises feeding the effluent to an absorption vessel wherein the effluent is intimately contacted with a water-miscible, liquid absorbent to obtain:

(1) a gaseous effluent comprising butadiene, oxygen and an inert diluent from the upper section of the absorption vessel; and (2) a liquid effluent comprising epoxybutene, the absorbent and water from the lower section of the absorption vessel;

wherein the absorbent is selected from diols, aliphatic and cyclic ethers, alkoxyalkanols, alkanoate esters of alkoxyalkanols, dialkoxyalkanes, alkylnitriles, N,N-dialkylformamides, N,N-dialkylacetamides, N-alkylpyrrolidinones, dialkyl sulfoxides, morpholine, pyridine, or a mixture of any 2 or more thereof and the extractent compound(s) contain 3 to 8 carbon atoms; epoxybutene is 3,4-epoxy-1-butene; and butadiene is 1,3-butadiene.

2. Process according to claim 1 wherein the absorption vessel is operated at a temperature of about 5 to 60° C. and a pressure of about 2.5 to 7.5 bars absolute, the substantially-gaseous effluent is fed to the lower section of the absorption vessel, the absorbent is fed to the upper section of the absorption vessel, and liquid effluent (2) comprises about 5 to 20 weight percent epoxybutene.

3. Process according to claim 2 wherein the absorbent is 3-butene-1,2-diol or 1-methyl-2-pyrrolidinone.

4. Process according to claim 1 wherein gaseous effluent (1) is fed to a water wash column to produce a liquid effluent comprising water and absorbed water-miscible absorbent and a gaseous effluent comprising butadiene, oxygen, inert diluent and less 50 ppmv water-miscible absorbent and the gaseous effluent is recycled to an epoxidation zone wherein butadiene is oxidized to epoxybutene.

5. Process according to claim 1 for the recovery of epoxybutene from the liquid effluent (2) of claim 1 by the steps of:

I. feeding liquid effluent (2) to the middle section of a first distillation column to obtain (1) a distillate effluent comprising epoxybutene and water from the upper section of the absorption vessel; and (2) a liquid effluent comprising the extractant and water from the lower section of the distillation vessel;

II. allowing distillate (1) from step I to form 2 phases comprising an epoxybutene-rich phase and a water-rich phase; and III. feeding the epoxybutene/water phase from step II to the upper section of a second distillation column to obtain (1) a distillate effluent comprising epoxybutene and water from the upper section of the absorption vessel; and (2) a liquid effluent comprising the epoxybutene from the lower section of the absorption vessel.

6. Process according to claim 5 wherein the first distillation column is operated at a top temperature of about 60 to 105° C. and a base temperature of about 100 to 185° C. and a pressure of about 1 to 2.3 bars absolute and the second distillation column is operated at a top temperature of about 60 to 75° C. and a base temperature of about 67 to 120° C. and a pressure of about 1 to 2.3 bars absolute.

* * * * *

UNITED STATES PATENT AND TRADEMARK OFFICE
CERTIFICATE OF CORRECTION

PATENT NO. : 6,596,882 B2
DATED : July 22, 2003
INVENTOR(S) : Barnicki et al.

It is certified that error appears in the above-identified patent and that said Letters Patent is hereby corrected as shown below:

Column 13,
Line 42, "15" should be -- 16 --.
Line 43, "16" should be -- 17 --.
Line 44, "17" should be -- 18 --.

Column 14,
Line 22, after "line 29" and before the "." insert -- or line 4 --.
Line 33, "41" should be -- 42 --.

Column 15,
Line 23, "65" should be -- 63 --.

Signed and Sealed this

Twenty-ninth Day of June, 2004

JON W. DUDAS
*Acting Director of the United States Patent and Trademark Office*